United States Patent [19]

Draber et al.

[11] Patent Number: 4,785,002

[45] Date of Patent: Nov. 15, 1988

[54] IMIDAZO-PYRROLO-PYRIDINES USEFUL AS FUNGICIDAL AND GROWTH-REGULATING AGENTS

[75] Inventors: Wilfried Draber, Wuppertal; Gerd Hänssler, Leverkusen; Klaus Lürssen, Bergisch Gladbach, all of Fed. Rep. of Germany

[73] Assignee: Bayer Aktiengesellschaft, Leverkusen, Fed. Rep. of Germany

[21] Appl. No.: 914,090

[22] Filed: Oct. 1, 1986

[30] Foreign Application Priority Data

Oct. 1, 1985 [DE] Fed. Rep. of Germany ....... 3534948

[51] Int. Cl.$^4$ .................. A01N 43/40; C07D 487/14; C07D 487/20

[52] U.S. Cl. .................................... 514/293; 514/278; 514/63; 514/439; 546/17; 546/11; 546/271; 71/92

[58] Field of Search ........................... 546/17, 271, 14; 514/278, 439, 63, 293; 71/92

[56] References Cited

U.S. PATENT DOCUMENTS 4,565,566 1/1986 Draber et al. ................... 546/14

FOREIGN PATENT DOCUMENTS 0041623 12/1981 European Pat. Off. .
0133309 2/1985 European Pat. Off. .

Primary Examiner—Robert T. Bond
Attorney, Agent, or Firm—Sprung Horn Kramer & Woods

[57] ABSTRACT

A method of combating fungi or regulating the growth of plants which comprises applying to such fungi, such plants or to a fungus or plant growth situs an amount effective therefor of an imidazo-pyrrolo-pyridine of the formula

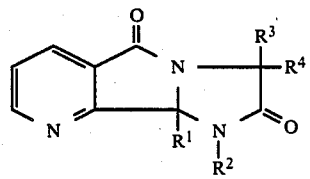

in which
R$^1$ represents cyano, alkoxycarbonyl or aminocarbonyl,
R$^2$ represents hydrogen, alkyl, trimethylsilyl or one equivalent of a metal cation and
R$^3$ and R$^4$ independently of one another each represent alkyl, cycloalkyl or cycloalkylalkyl or
R$^3$ and R$^4$ together represent a divalent alkanediyl radical.

Many of the compounds are new.

10 Claims, No Drawings

IMIDAZO-PYRROLO-PYRIDINES USEFUL AS FUNGICIDAL AND GROWTH-REGULATING AGENTS

The invention relates to the use of imidazopyrrolo-pyridines as fungicides and plant growth regulators.

Certain imidazo-pyrrolo-pyridines and their use as herbicides are already known (compare, for example, European Pat. No. 41,623 or European Pat. No. 133,309).

It is furthermore known that organic sulphur compounds, such as, for example, zinc ethylene-1,2-bis-(dithiocarbamate) have fungicidal properties (compare, for example, K. H. Büchel "Pflanzenschutz und Schädlingsbekämpfung" ("Plant protection and combating pests") page 137; G. Thieme Verlag Stuttgart 1977).

However, the activity of these already known sulphur compounds is not always completely satisfactory in all fields of use, especially when low amounts are applied and in the case of low concentrations.

It has now been found that imidazo-pyrrolo-pyridines of the general formula (I)

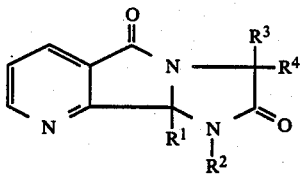

(I)

in which

R$^1$ represents cyano, alkoxycarbonyl or aminocarbonyl,

R$^2$ represents hydrogen, alkyl, trimethylsilyl or one equivalent of a metal cation and R$^3$ and R$^4$ independently of one another each represent alkyl, cycloalkyl or cycloalkylalkyl or R$^3$ and R$^4$ together represent a divalent alkanediyl radical, have good fungicidal and growth-regulating properties.

Surprisingly, the imidazo-pyrrolo-pyridines of the general formula (I) which can be used according to the invention have a considerably more powerful fungicidal activity than the orgaic sulphur compounds known from the prior art, such as, for example, zinc ethylene-1,2-bis-(dithiocarbamate), which is a closely related compound from the point of view of its action, and moreover unexpectedly are outstandingly suitable as plant growth regulators.

Formula (I) provides a general definition of the imidazo-pyrrolo-pyridines which can be used according to the invention. Preferred compounds of the formula (I) are those in which R$^1$ represents cyano, aminocarbonyl or straight-chain or branched alkoxycarbonyl with 1 to 4 carbon atoms in the alkoxy part, R$^2$ represents hydrogen or straight-chain or branched alkyl with 1 to 4 carbon atoms, or represents trimethylsilyl, or represents one equivalent of an alkali metal or alkaline earth metal cation and R$^3$ and R$^4$ independently of one another each represent straight-chain or branched alkyl with 1 to 6 carbon atoms, or represent cycloalkyl with 3 to 7 carbon atoms, or represent a cycloalkylalkyl which has 3 to 7 carbon atoms in the cycloalkyl part and 1 to 4 carbon atoms in the alkyl part and is straight-chain or branched in the alkyl part, or R$^3$ and R$^4$ together represent a divalent alkanediyl radical with 4 to 6 carbon atoms. Particularly preferred imidazo-pyrrolo-pyridines of the formula (I) are those in which R$^1$ represents cyano, aminocarbonyl, methoxycarbonyl, ethoxycarbonyl, n-propoxycarbonyl, i-propoxycarbonyl or n-butoxycarbonyl, R$^2$ represents hydrogen, methyl, ethyl, n-propyl, i-propyl or trimethylsilyl, or represents a sodium or a potassium ion and R$^3$ and R$^4$ independently of one another each represent methyl, ethyl, n-propyl, i-propyl, n-butyl, i-butyl, s-butyl, t-butyl, cyclopropyl, cyclopentyl, cyclohexyl, cyclopropylmethyl, cyclopentylmethyl or cyclohexylmethyl or R$^3$ and R$^4$ together represent 1,4-butanediyl, 1,5-pentanediyl or 1,6-hexanediyl.

The compounds described in the preparation examples may be mentioned specifically.

The imidazo-pyrrolo-pyridines which can be used according to the invention are not yet known. Some of them are the subject of a Patent Application which has been filed by the Application Company and has not yet been published (compare German Pat. No. 3,520,390.0 of 7.6.1985).

They are obtained by a process in which imidazo-pyrrolo-pyridines of the formula (II)

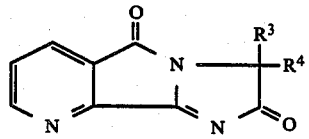

(II)

in which

R$^3$ and R$^4$ have the abovementioned meaning, are reacted with trimethylsilyl cyanide of the formula (III)

(CH$_3$)$_3$Si—CN  (III)

if appropriate in the presence of a diluent, such as, for example, ligroin or methylene chloride, at temperatures between 20° C. and 150° C., to give compounds of the formula (Ia), and, if appropriate, the imidazo-pyrrolo-pyridines thus obtainable, of the formula (Ia)

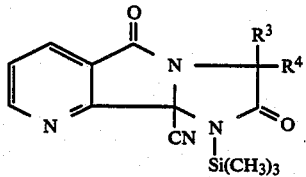

(Ia)

in which

R$^3$ and R$^4$ have the abovementioned meanings, are further hydrolyzed with hydroxy compounds of the formula (IV)

R$^5$—OH  (IV)

in which $R^5$ represents hydrogen or alkyl, if appropriate in the presence of a diluent, such as, for example, methylene chloride, and if appropriate in the presence of a catalyst, such as, for example, sulphuric acid or hydrochloric acid, at temperatures between 20° C. and 100° C. If appropriate, the compounds thus obtained can then be alkylated by customary processes with alkylating agents of the formula (V)

$$R^{2'}-X \qquad (V)$$

in which $R^{2'}$ represents alkyl and

X represents a leaving group, such as, for example, halogen (in particular bromine or iodine) or optionally substituted alkoxysulphonyloxy or arylsulphonyloxy (in particular methoxysulphonyloxy or p-toluenesulphonyloxy), if appropriate in the presence of a diluent, such as, for example, acetonitrile or methanol, and if appropriate in the presence of a basic catalyst, such as, for example, sodium methylate, at temperatures between 20° C. and 100° C., or can form a salt by customary methods, for example with alkali metal or alkaline earth metal hydroxides, if appropriate in the presence of a diluent, such as, for example, methanol, at temperatures between 0° C. and 80° C.

Imidazo-pyrrolo-pyridines which can be used according to the invention and which have not yet been described are those of the formula (Ib)

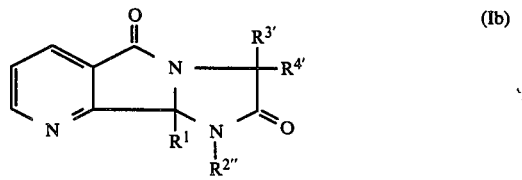

in which $R^1$ has the meanings given above in the case of formula (I), $R^{2''}$ represents alkyl, preferably alkyl with 1 to 4 carbon atoms, in particular methyl, ethyl, n-propyl or iso-propyl, or represents one equivalent of a metal cation, preferably an alkali metal or alkaline earth metal cation, in particular a sodium or potassium ion, and $R^{3'}$ and $R^{4'}$ independently of one another each represent alkyl, cycloalkyl or cycloalkylalkyl, and preferably represent alkyl with 1 to 6 carbon atoms, in particular methyl, ethyl, n-propyl, iso-propyl, n-butyl, iso-butyl, s-butyl or t.-butyl, or represent cycloalkyl with 3 to 7 carbon atoms, in particular cyclopropyl, cyclopentyl or cyclohexyl, or represent cycloalkylalkyl with 3 to 7 carbon atoms in the cycloalkyl part and 1 to 4 carbon atoms in the alkyl part, in particular cyclopropylmethyl, cyclopentylmethyl or cyclohexylmethyl, and those of the formula (Ic)

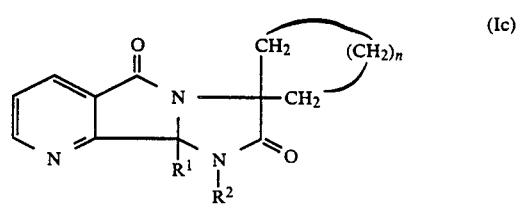

in which $R^1$ and $R^2$ have the meanings given above in the case of formula (I) and n represents the number 2, 3, or 4.

The imidazo-pyrrolo-pyridines of the formulae (Ib) and (Ic) are obtained with the aid of the process described above, by a procedure in which imidazo-pyrrolo-pyridines of the formulae (IIb) or (IIc)

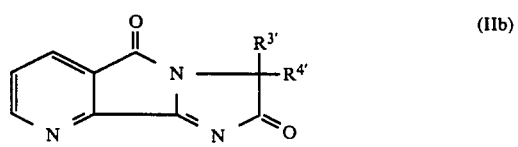

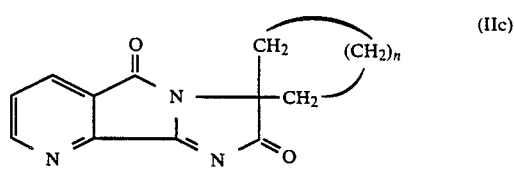

in which $R^{3'}$ and $R^{4'}$ have the abovementioned meanings, are reacted with trimethylsilyl cyanide of the formula (III) to give the compounds of the formulae (Ib') and (Ic')

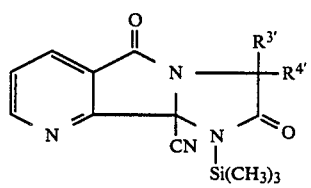

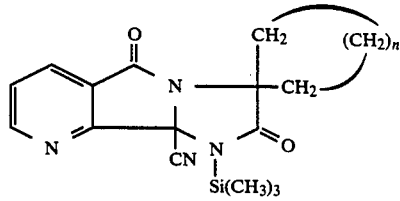

wherein $R^{3'}$, $R^{4'}$ and n have the abovementioned meanings, and these are further reacted, as stated for the compounds of the formula (I), that is to say first with compounds of the formula (IV) and then with compounds of the formula (V) or with alkali metal or alkaline earth metal hydroxides.

The starting substances of the formula (II) required for this are known (compare European Pat. No. 41,623). The starting substances of the formulae (III), (IV) and (V) are generally known compounds of organic chemistry.

The active compounds which can be used according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadeceae, Rhizobiaceae, Enterobacteriaceae, Corynebacteriaceae and Streptomycetaceae.

Some pathogens of fungal and bacterial diseases which fall under the generic names listed above may be mentioned as examples but not by way of limitation: Xanthomonas species, such as, for example, *Xanthomonas campestris* pv. oryzae; Pseudomonas species, such as, for example, *Pseudomonas syringae* pv. Lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Utilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds which can be used according to the invention can be used with particularly good success for comating rice diseases, such as, for example, against the rice spot disease causative organism (*Pyricularia oryzae*).

Moreover, the active compounds which can be used according to the invention also show a very good systemic activity, in addition to outstanding protective properties.

The substances which can be used according to the invention moreover also exhibit a bactericial activity.

The active compounds which can be used according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibiton of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent that they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is undestood the peculiarity of some varieties of fruit to produce very different yields from year to year, for endogenic reasons. Finally, using growth regulators it is possible to reduce the forces required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can in some cases improve the coloration of fruit. In addition, concentration the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting or buds or the germination of seeds with the aid of growth regulators can be desirable in regions where frost is a hazard, in order to avoid damage by last frosts.

Finally, resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore to formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersng agents there are suitable: for example ligninsulphite waste liquors and methylcellulose.

Adhesives such as carboxymethylcellulose and natural and synthetic polymers in the form of powders, granules or latice, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, bactericides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

When used as fungicides, in the treatment of parts of plants the active compound concentrations in the use forms can be varied within a substantial range. They are, in general, between 1 and 0.001% by weight, preferably between 0.5 to 0.001%.

In the treatment of seed, amounts of active compound of 0.001 to 50 g per kilogram of seed, preferably 0.01 to 10 g, are generally required.

For the treatment of soil, active compound concentrations of 0.00001 to 1.0% by weight, preferably 0.0001 to 0.02% by weight, are required at the place of action.

When used as growth regulators, the amounts applied can be varied within a substantial range. In general, 0.01 to 50 kg, preferably 0.5 to 10 kg, of active compound are used per hectare of soil surface.

As regards the time of application, the growth regulators are applied within a preferred period of time, the exact definition of which depends on the climatic acid vegetative circumstances.

PREPARATION EXAMPLES

Example 1

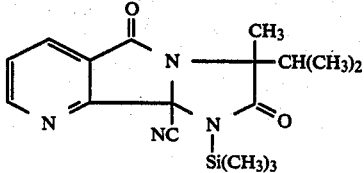

A mixture of 24.3 g (0.1 mole) of 3-isopropyl-3-methyl-5H-imidazo-[1',2':1,2]pyrrolo[3,4-b]-pyridine-2-(3H),5-dione and 100 ml (79 g, about 1 mole) of trimethylsilyl cyanide is stirred at a bath temperature of 100° C. for 16 hours, cooled and concentrated and the volatile constituents are removed under a high vacuum.

34 g (100% of theory) of the compound of the formula given above are obtained as an oil.

IR (cm$^{-1}$): 2200 (—CN, very weak), 1730

(—C—).

NMR (60 MHZ; ppm/TMS as an internal standard): 9H, 0.32 (Si(CH$_3$)$_3$); 11H, 0.55, 0.12, 1.5, 2.0 (CH$_3$ and CH(CH$_3$)$_2$); 3H, 7.5, 8.1, 8.9 (pyridine protons).

MS (chemical ionization with NH$_3$): 343 (M+I), 299 (M+2—CH(CH$_3$)$_2$), 299, (M+I—(CH(CH$_3$)$_2$—CN):
IR=infrared spectrum;
NMR=nuclear magnetic resonance spectrum (TMS=tetramethylsilane, (CH$_3$)$_4$Si);
MS=mass spectrum (M=molecular ion).

Example 2

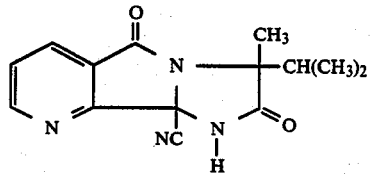

34.2 g (0.1 mole) of the compound from Example 1, 400 ml of ligroin, 100 ml of methylene chloride and 2.5 ml (0.14 mole) of water are stirred at room temperature (20° C. to 25° C.) for 12 to 15 hours, the mixture is filtered, the filtrate is evaporated and the residue is stirred with ether and filtered off with suction. The crude product thus obtained is chromatographed on a silica gel column (mobile phase: cyclohexane/ethyl acetate 1:1).

22.5 g (83% of theory) of the compound of the formula shown above of melting point 155° C. (decomposition) are obtained.

EXAMPLE 3

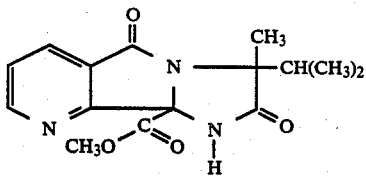

20.2 g (0.075 mole) of the compound from Example 2, 200 ml of methylene chloride, 12 g (0.375 mole) of methanol and 40 ml of concentrated hydrochloric acid are boiled under reflux for 24 hours, the mixture is cooled and concentrated in vacuo, the residue is taken up in ethyl acetate and the mixture is washed with water, dried over sodium sulphate and concentrated in vacuo. The oil which remains is chromatographed over a silica gel column (mobile phase: chloroform/ethyl acetate/methanol-10:10:2).

6.4 g (28% of theory) of the compound of the formula shown above of melting point 196° C. are obtained.

Example 4

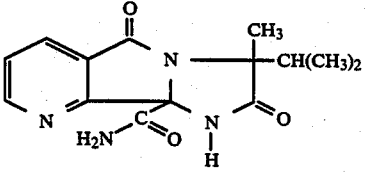

8.1 g (0.03 mole) of the compound from Example 2, 6 g (0.06 mole) of concentrated sulphuric acid, 1 ml (0.055 mole) of water and 0.17 g (0.003 mole) of sodium chloride are stirred at 40° C. to 50° C. for 4 hours. Thereafter, 50 ml of methanol are added and the mixture is stirred at 50° C. for a further 3 hours and at room temperature for 12 hours (20° C. to 25° C.). For working up, the mixture is diluted with 50 ml of water and neutralized with sodium bicarbonate and the solid which has precipitated out is filtered off with suction and dried.

3.2 g (37% of theory) of the compound of the formula shown above of melting point 281° C. (decomposition) are obtained.

The following imidazo-pyrrolo-pyridines of the formula (I) are obtained in a corresponding manner and in accordance with the general preparation statements:

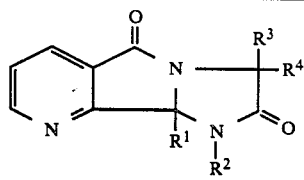
(I)

| Example No. | | physical properties |
| --- | --- | --- |
| 5 | | Melting point 176° C. |
| 6 | | Melting point 167° C. |
| 7 | | Melting point 295° C. |
| 8 | | Melting point 265° C. |
| 9 | | Melting point 160° C. |
| 10 | | Melting point 226° C. |
| 11 | | Melting point 180–250° C. (×2 H₂O) |

-continued
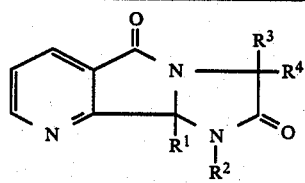 (I)
| Example No. | | physical properties |
|---|---|---|
| 12 | 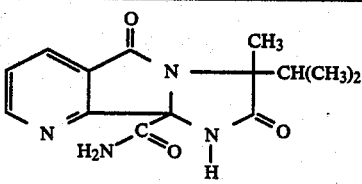 | Melting point 285° C. |
| 13 | 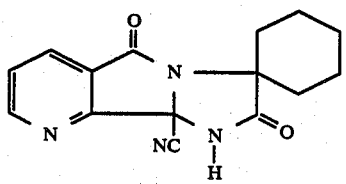 | Melting point 174° C. |
| 14 | 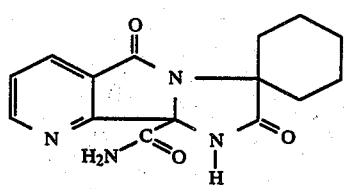 | Melting point 301° |
| 15 | 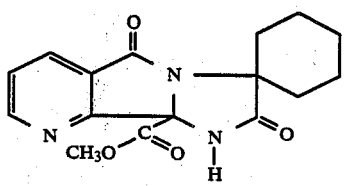 | Melting point 184° |
| 16 | 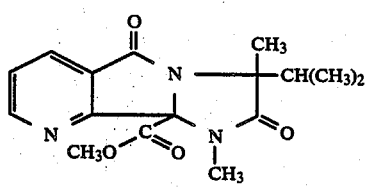 | Melting point 142° C. |
| 17 | 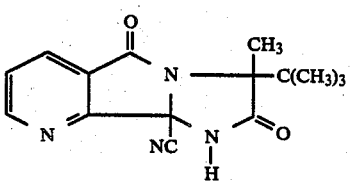 | Melting point 168° C. |
Use Examples
The compound shown below was used as a comparison substance in the use example which follows:

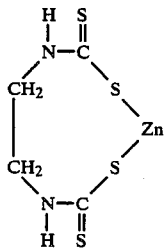

(A) and a relative atmospheric humidity of 100% until they are evaluated.

Evaluation of the disease infestation is carried out 4 days after the inoculation.

In this test, a clearly superior activity compared with the prior art is shown, for example, by the compound according to preparation Example 3.

TABLE A

Pyricularia test (rice)/systemic

| Active compounds | Amount applied in mg of active compound per 100 cm$^2$ | Disease infestation in % of the untreated control |
|---|---|---|
| (A) (known) | 100 | 100 |
| (3) | 100 | 20 |

Zinc ethylene-1,2-bis-(dithiocarbamate) (known from K. H. Büchel "Pflanzenschutz und Schädlingsbekäampfung" ("Plant protection and combating pests") page 137, Thieme Verlag Stuttgart 1977).

Example A

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C.

Example B

Growth of barley

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvents and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and is calculated in percent of the additional growth of the control plants. 100% denotes an additional growth as in the controls, values below 100% represent inhibition of growth and values above 100% represent promotion of growth.

In this test, a clear activity in comparison with untreated controls is shown, for example, by the compound according to preparation Example 4.

TABLE C

Growth of barley

| Active compound | Concentration in % | Growth in % |
|---|---|---|
| untreated control | — | 100 |

TABLE C-continued

| Growth of barley | | |
|---|---|---|
| Active compound | Concentration in % | Growth in % |
| 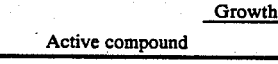 (4) | 0.05 | 65 |

It will be understood that the specification and examples are illustrative but not limitative of the present invention and that other embodiments within the spirit and scope of the invention will suggest themselves to those skilled in the art.

What is claimed:

1. A method of combating fungi or regulating the growth of plants which comprises applying to such fungi, such plants or to a fungus or plant growth situs an amount effective therefor of an imidazo-pyrrolo-pyridine of the formula

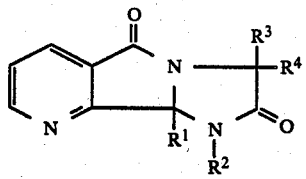

in which,
R$^1$ represents cyano, aminocarbonyl or straight-chain or branched alkoxycarbonyl with 1 to 4 carbon atoms in the alkoxy part,
R$^2$ represents hydrogen or straight-chain or branched alkyl with 1 to 4 carbon atoms, or represents trimethylsilyl, or represents one equivalent of an alkali metal or alkaline earth metal cation, and
R$^3$ and R$^4$ independently of one another each represent straight-chain or branched alkyl with 1 to 6 carbon atoms, or represent cycloalkyl with 3 to 7 carbon atoms, or represent a cycloalkylalkyl which has 3 to 7 carbon atoms in the cycloalkyl part and 1 to 4 carbon atoms in the alkyl part and is straight-chain or branched on the alkyl part, or
R$^3$ and R$^4$ together represent a divalent alkanediyl radical with 4 to 6 carbon atoms.

2. A method according to claim 1, in which
R$^1$ represents cyano, aminocarbonyl, methoxycarbonyl, ethoxycarbonyl, n-propoxycarbony, i-propoxycarbonyl or n-butoxycarbonyl,
R$^2$ represents hydrogen, methyl, ethyl, n-propyl, i-propyl or trimethylsilyl, or represents a sodium or a potassium ion and
R$^3$ and R$^4$ independently of one another each represent methyl, ethyl, n-propyl, i-propyl, n-butyl, i-butyl, s-butyl, t-butyl, cyclopropyl, cyclopentyl, cyclohexyl, cyclopropylmethyl, cyclopentylmethyl or cyclohexylmethyl or
R$^3$ and R$^4$ together represent 1,4-butanediyl, 1,5-pentanediyl or 1,6-hexanediyl.

3. A method according to claim 1, wherein the compound is applied to a fungus or a fungus habitat.

4. A method according to claim 1, wherein the compound is applied to a plant or to a locus in which a plant is growing or is to be grown.

5. A method according to claim 1, in which
R$^1$ represents cyano, aminocarbonyl or straight-chain or branched alkoxycarbonyl with 1 to 4 carbon atoms in the alkoxy part,
R$^2$ represents straight-chain or branched alkyl with 1 to 4 carbon atoms, or represents one equivalent of an alkali metal or alkaline earth metal cation and,
R$^3$ and R$^4$ independently of one another each represent straight-chain or branched alkyl with 1 to 6 carbon atoms, or represent cycloalkyl with 3 to 7 carbon atoms, or represent cycloalkylalkyl which has 3 to 7 carbon atoms in the cycloalkyl part and 1 to 4 carbon atoms in the alkyl part and is straight-chain or branched in the alkyl part.

6. A method according to claim 1, in which
R$^1$ represents cyano, aminocarbonyl or straight-chain or branched alkoxycarbonyl with 1 to 4 carbon atoms in the alkoxy part,
R$^2$ represent hydrogen or straight-chain or branched alkyl with 1 to 4 carbon atoms or represents trimethylsilyl, or represents one equivalent of an alkali metal or alkaline earth metal cation, and
R$^3$ and R$^4$ together represent butanediyl, pentanediyl or hexanediyl.

7. A method according to claim 1, wherein the compound is of the formula

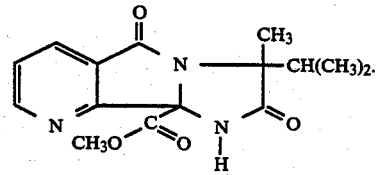

8. A method according to claim 1, wherein the compound is of the formula

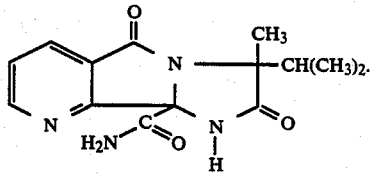

9. An imidazo-pyrrolo-pyridine of the formula

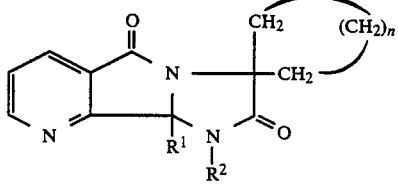 (Ic)

in which
R¹ represents cyano, aminocarbonyl or straight-chain or branched alkoxycarbonyl with 1 to 4 carbon atoms in the alkoxy part,
R² represents hydrogen or straight-chain or branched alkyl with 1 to 4 carbon atoms or represents trimethylsilyl, or represents one equivalent of an alkali metal or alkaline earth metal cation and
n represents the number 2, 3 or 4.

10. A fungicidal or plant growth-regulating composition comprising a fungicidally or plant growth regulating effective amount of a compound of the formula

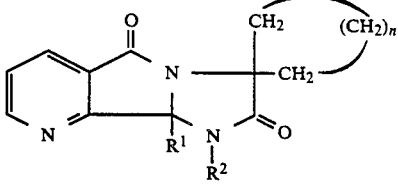 (Ic)

wherein R¹ represents cyano, aminocarbonyl or straight or branched alkoxycarbonyl with 1 to four carbon atoms in the alkoxy part and R² represents alkyl having 1 to 4 carbon atoms or represents one equivalent of a metal cation; and a diluent.

* * * * *